United States Patent [19]

Takahashi et al.

[11] Patent Number: 5,184,170
[45] Date of Patent: Feb. 2, 1993

[54] PHOTOGRAPHING LIGHT QUANTITY CONTROLLER FOR ENDOSCOPE

[75] Inventors: Tadashi Takahashi; Katsuhiko Furuya; Masaaki Nakasima; Takayuki Enomoto, all of Tokyo, Japan

[73] Assignee: Asahi Kogaku Kogyo Kabushiki Kaisha, Tokyo, Japan

[21] Appl. No.: 596,382

[22] Filed: Oct. 12, 1990

[30] Foreign Application Priority Data

Oct. 16, 1989 [JP] Japan .................................. 1-270083
Feb. 14, 1990 [JP] Japan .................................. 2-33216
Jul. 26, 1990 [JP] Japan .................................. 2-20055

[51] Int. Cl.⁵ .............................................. G03B 7/00
[52] U.S. Cl. ................................... 354/413; 354/62
[58] Field of Search ............................. 354/410–424, 354/62; 128/4, 6

[56] References Cited

U.S. PATENT DOCUMENTS

| | | | |
|---|---|---|---|
| 4,021,663 | 5/1977 | Takahashi | 128/4 |
| 4,322,129 | 3/1982 | Takahashi et al. | 128/6 |
| 4,366,529 | 12/1982 | Takahashi et al. | 362/4 |
| 4,561,429 | 12/1985 | Sato et al. | 354/62 X |
| 4,872,029 | 10/1989 | Kato | 354/62 |
| 4,945,336 | 7/1990 | Hisamichi et al. | 354/62 |

FOREIGN PATENT DOCUMENTS

| | | |
|---|---|---|
| 0018126 | 10/1980 | European Pat. Off. |
| 58-94829 | 6/1983 | Japan |
| 58-97355 | 6/1983 | Japan |
| 61-36928 | 8/1986 | Japan |
| 2-84609 | 3/1990 | Japan |

Primary Examiner—Michael L. Gellner
Assistant Examiner—Daivd M. Gray
Attorney, Agent, or Firm—Sandler, Greenblum & Bernstein

[57] ABSTRACT

A photographing light quantity controller for an endoscope is used to control the quantity of illuminating light when a photograph is to be taken through the endoscope. The photographing light quantity controller comprises a light source for supplying light for illuminating an object to the endoscope, and a device for detecting an illuminating condition in an observation state before a photographing operation is initiated. A device is also provided for controlling the brightness of illuminating light that is supplied from the light source to the endoscope during the photographing operation on the basis of a signal that is detected by the device for detecting an illuminating condition in the observation state.

18 Claims, 16 Drawing Sheets

FIG. 4

| EXPOSURE IND. EI | 0 | 1 | 2 | 3 | 4 | 5 | 6 | 7 | 8 | 9 |
|---|---|---|---|---|---|---|---|---|---|---|
| EXPOSURE QUANTITY (RELATIVE VALUE) | $2^{\frac{5}{2}}$ | $2^{2}$ | $2^{\frac{3}{2}}$ | $2^{1}$ | $2^{\frac{1}{2}}$ | 1 | $2^{-\frac{1}{2}}$ | $2^{-1}$ | $2^{-\frac{3}{2}}$ | $2^{-2}$ |
| REF. VOLTAGE Vr | -5.7 | 4.0 | 2.8 | 2.0 | 1.4 | 1.0 | 0.71 | 0.50 | 0.35 | 0.25 |

FIG.11

| EXPOSURE IND. EI | 0 | 1 | 2 | 3 | 4 | 5 | 6 | 7 | 8 | 9 |
|---|---|---|---|---|---|---|---|---|---|---|
| EXPOSURE QUANTITY (RELATIVE VALUE) | $2^{\frac{5}{2}}$ | $2^2$ | $2^{\frac{3}{2}}$ | $2^1$ | $2^{\frac{1}{2}}$ | 1 | $2^{-\frac{1}{2}}$ | $2^{-1}$ | $2^{-\frac{3}{2}}$ | $2^{-2}$ |
| Te NUMBER | 20 | 18 | 16 | 14 | 12 | 10 | 8 | 6 | 4 | 2 |

FIG. 12

| BRIGHTNESS IND. BI | 0 | 1 | 2 | 3 | 4 | 5 | 6 | 7 | 8 | 9 |
|---|---|---|---|---|---|---|---|---|---|---|
| BRIGHTNESS (RELATIVE VALUE) | $2^{\frac{5}{2}}$ | $2^{-2}$ | $2^{-\frac{3}{2}}$ | $2^{-1}$ | $2^{-\frac{1}{2}}$ | $2^1$ | $2^{\frac{1}{2}}$ | $2^1$ | $2^{\frac{3}{2}}$ | $2^2$ |
| Tb NUMBER | 1 | 2 | 3 | 4 | 5 | 6 | 7 | 8 | 9 | 10 |

PHOTOGRAPHING LIGHT QUANTITY CONTROLLER FOR ENDOSCOPE

BACKGROUND OF THE INVENTION

1. Field of the Invention

The present invention relates to a photographing light quantity controller for an endoscope, which is used to control the quantity of illuminating light when a photograph is to be taken through the endoscope.

Endoscopes are generally designed to be capable of not only observing the inside of a hollow organ in the patient's body but also taking a photograph of it.

When a photograph is to be taken through an endoscope, the brightness (luminous flux) of illuminating light that is supplied to the endoscope is set to a maximum level and, in this state, the output of a light-receiving element that receives the reflected light from an object is integrated; when the integral output voltage reaches a reference voltage, a mechanical shutter that is provided in an illuminating light path within a light source device is closed, thereby controlling the exposure time.

However, such a mechanical shutter takes some time from the instant it receives a signal for closing until it has been completely closed, and the exposure therefore becomes correspondingly excessive. The exposure time $\Delta T$ that corresponds to an excess of exposure is constant independently of the length of the overall exposure time on each particular occasion. Accordingly, when the overall exposure time T is relatively short, that is, when the object is relatively bright as in the case of close-up photography, the effect of $\Delta T$ becomes significant, resulting in a high degree of over-exposure.

2. Description of the Prior Art

To reduce the degree of over-exposure, a method has heretofore been employed in which the rise of a signal representative of an integral state value which is obtained by integrating the output of a light-receiving element is detected differentially, and when the differential output value is greater than a reference value, the brightness of a light source is lowered to an observational state level to increase the overall exposure time T, thereby reducing the effect of $\Delta T$.

However, even if such an over-exposure control measure is taken, some problems still remain unsolved. For example, the illuminating light flux is set one set to a maximum level at the time of photographing, thus a picture is taken at an extremely short distance to the object, or when a fast film is employed, the correction of the illuminating light flux cannot be effectively made, and over-exposure is unavoidable. In addition, since the brightness of the illuminating light is merely lowered to a level for the observation after the correction, no delicate control can be effected, so that the exposure time may become excessively long, resulting in blurring or other problems.

SUMMARY OF THE INVENTION

An object of the present invention is to provide a photographing light quantity controller for an endoscope, which is capable of delicately controlling the brightness of illuminating light during a photographing operation to prevent both over-exposure and blur, hence effecting ideal exposure control.

Other objects and advantages of the present invention will become apparent from the following detailed description of illustrated embodiments of the invention.

According to the present invention, there is provided a photographing light quantity controller for an endoscope, which is used to control the quantity of illuminating light when a photograph is to be taken through the endoscope; A light source is provided for supplying light to illuminate an object to the endoscope; a device detects an illuminating condition in an observation state before a photographing operation is initiated, and another device controls the brightness of illuminating light that is supplied from the light source to the endoscope during the photographing operation on the basis of a signal that is detected by the device for detecting an illuminating condition in the observation state.

In accordance with another aspect of the present invention, a photographing apparatus is provided having a light source, a switch device, a detecting device, and a control device. The light source supplies light for illuminating an object to be photographed by the photographing apparatus. The switch device initiates and synchronizes a photographing operation of the photographing apparatus by, e.g., activating a plurality of operations of the apparatus pertaining to the photographing operation. The detecting device detects an illuminating condition before a photographing operation is initiated and synchronized by the switch device. The control device is provided to control the brightness of illuminating light that is supplied from the light source to the photographing apparatus during the photographing operation on the basis of a signal that is detected by the detecting device.

BRIEF DESCRIPTION OF THE DRAWINGS

The present invention may be more fully understood from the description of preferred embodiments of the invention set forth below, together with the accompanying drawings, in which:

FIG. 4 is a chart showing one example of the setting of a reference voltage in the first embodiment;

FIGS. 11 and 12 are charts showing examples of the setting of an exposure index and a brightness index in the third embodiment;

DESCRIPTION OF THE EMBODIMENTS

Figure 1:
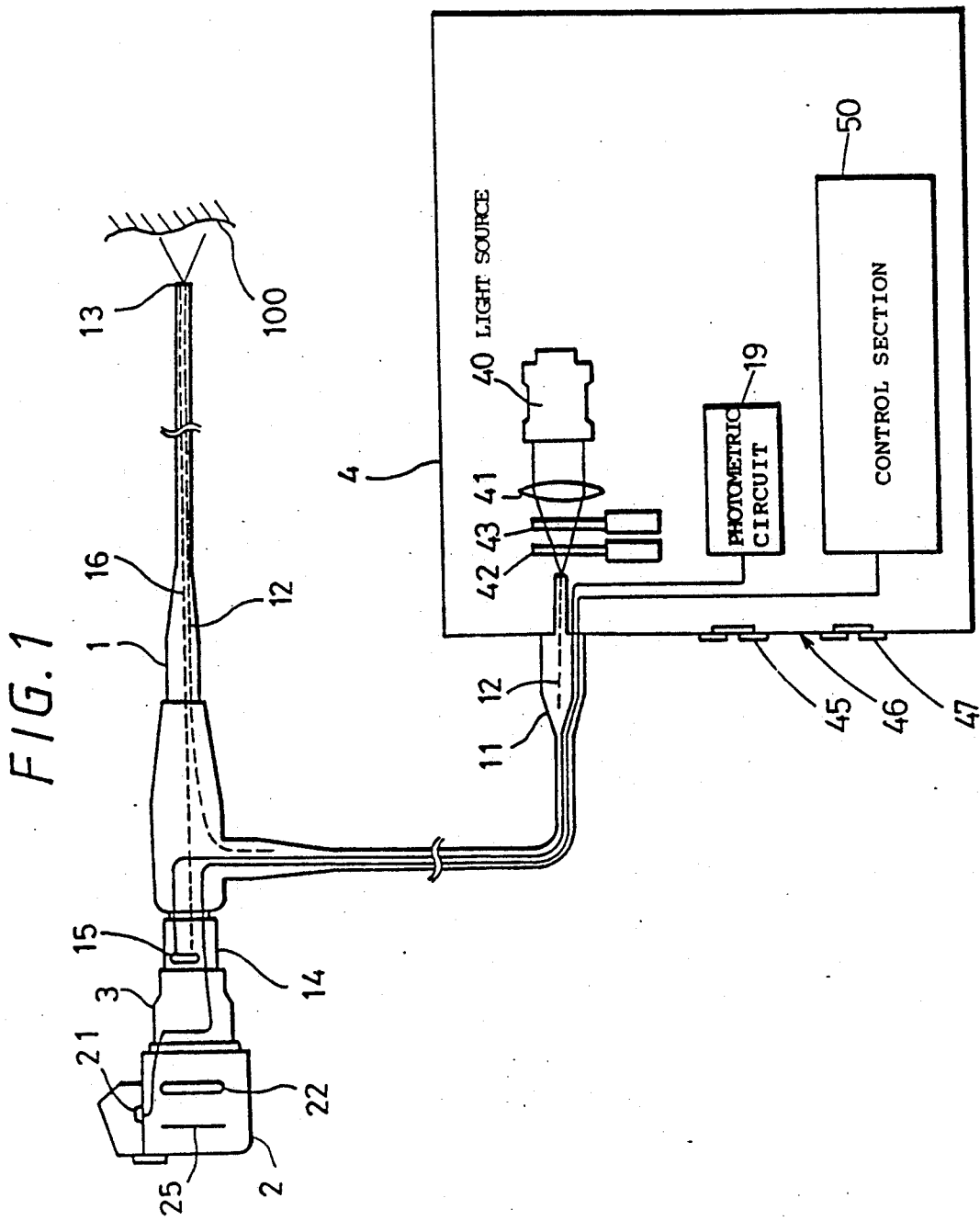
FIG. 1 is a schematic view showing the a complete arrangement of a first embodiment of the present invention.

Referring to FIG. 1, which shows the whole arrangement of a first embodiment of the present invention, reference numeral 1 denotes an endoscope. A camera (photographing device) 2 is detachably attached to an eyepiece 14 of the endoscope 1 through a photographic adapter 3.

Reference numeral 4 denotes a light source apparatus, to which is detachably connected a connector 11 of the endoscope 1. Illuminating light that is emitted from a light source (lamp) 40 is condensed through a condenser lens 41 and then transmitted through a light guide fiber bundle 12 in the endoscope 1.

In an illuminating light path which extends between the light source 40 and the light guide fiber bundle 12 are provided a shutter (light source shutter) 42 which can be opened and closed to fully open or close the illuminating light path, and a variable diaphragm 43 which is capable of varying the area of passage of the illuminating light.

The illuminating light is transmitted through the light guide fiber bundle 12 and applied to an object 100 from the distal end 13 of an insert part of the endoscope 1. The reflected light from the object 100 is transmitted through an image guide fiber bundle 16 to expose the plane (photographic plane) of a film 25 in the camera 2. A shutter 22 in the camera 2 is opened for a predetermined time (e.g., 0.25 sec) only when a synchro switch 21 is turned on.

A light-receiving element 15 is provided in the eyepiece 14 to convert a brightness level of the exposure light that is applied to the plane of the film 25 into an electric signal. The output voltage from the light-receiving element 15 is integrated in a photometric (integration) circuit 19, and an integral state value is outputted from the photometric circuit 19. The photometric circuit 19 may be provided in either the light source apparatus 4 or the endoscope 1.

An exposure index setting switch 45 is provided on an operation panel 46 that is attached to the surface of the light source apparatus 4 to set an exposure index that determines a quantity of light which is to be applied to the photographic plane 25 in the camera 2. A brightness setting switch 47 is used to set a brightness level of illuminating light that is supplied to the endoscope 1 when used in an observation state.

Reference numeral 50 denotes a control section which incorporates a central processing unit (CPU).

Figure 2:
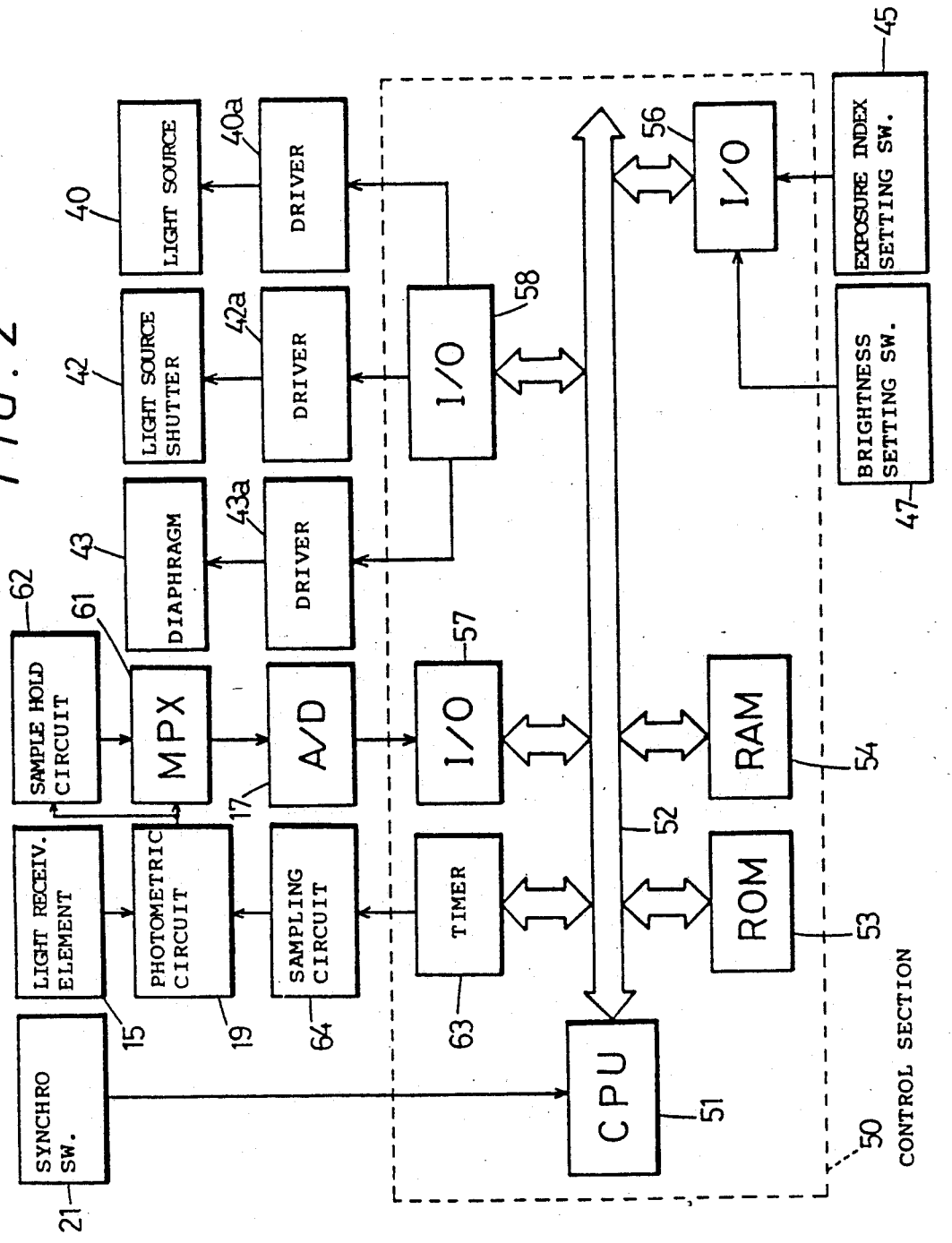
FIG. 2 is an electric circuit block diagram of the first embodiment.

FIG. 2 is a block diagram showing the electrical arrangement of the first embodiment. The control section 50 includes the CPU 51, and a read only memory (ROM) 53 and a random access memory (RAM) 54 are connected to the CPU 51 through a system bus 52. The CPU 51 is supplied with an interrupt signal which is outputted from the synchro switch 21.

The system bus 52 is further connected with first to third input/output ports 56, 57 and 58. The exposure index setting switch 45 and the brightness setting switch 47 are connected to the input terminal of the first input/output port 56.

The output from the light-receiving element 15 is integrated in the photometric (integration) circuit 19 to obtain an integral state value (integral output voltage V), which is input to the second input/output port 57 via a multiplexer 61 and an analog-to-digital converter 17.

The integral output of the photometric circuit 19 is also input to a sample-and-hold circuit 62 so that during observation, the peak value of the integral output voltage that is sampled in the sample-and-hold circuit 62 is selected in the multiplexer 61 and inputted to the second input/output port 57.

A clock signal that is outputted from a timer 63 that is connected to the system bus 52 is input to a sampling circuit 64, so that a sampling pulse is output from the sampling circuit 64 to the photometric circuit 19 in synchronism with the clock signal. During the observation, when the sampling pulse is at a low "0" level, the photometric circuit 19 performs an integral operation, whereas, when the sampling pulse is at a high "1" level, the integral output is zero (i.e., $V=0$). The sampling frequency is set, for example, at about 500 Hz.

The output terminal of the third input/output port 58 is connected to drivers 40a, 42a and 43a which control the brightness of light that is emitted from the light source 40, the opening and closing operation of the light source shutter 42, and the degree of opening of the variable diaphragm 43, respectively.

Figure 3:
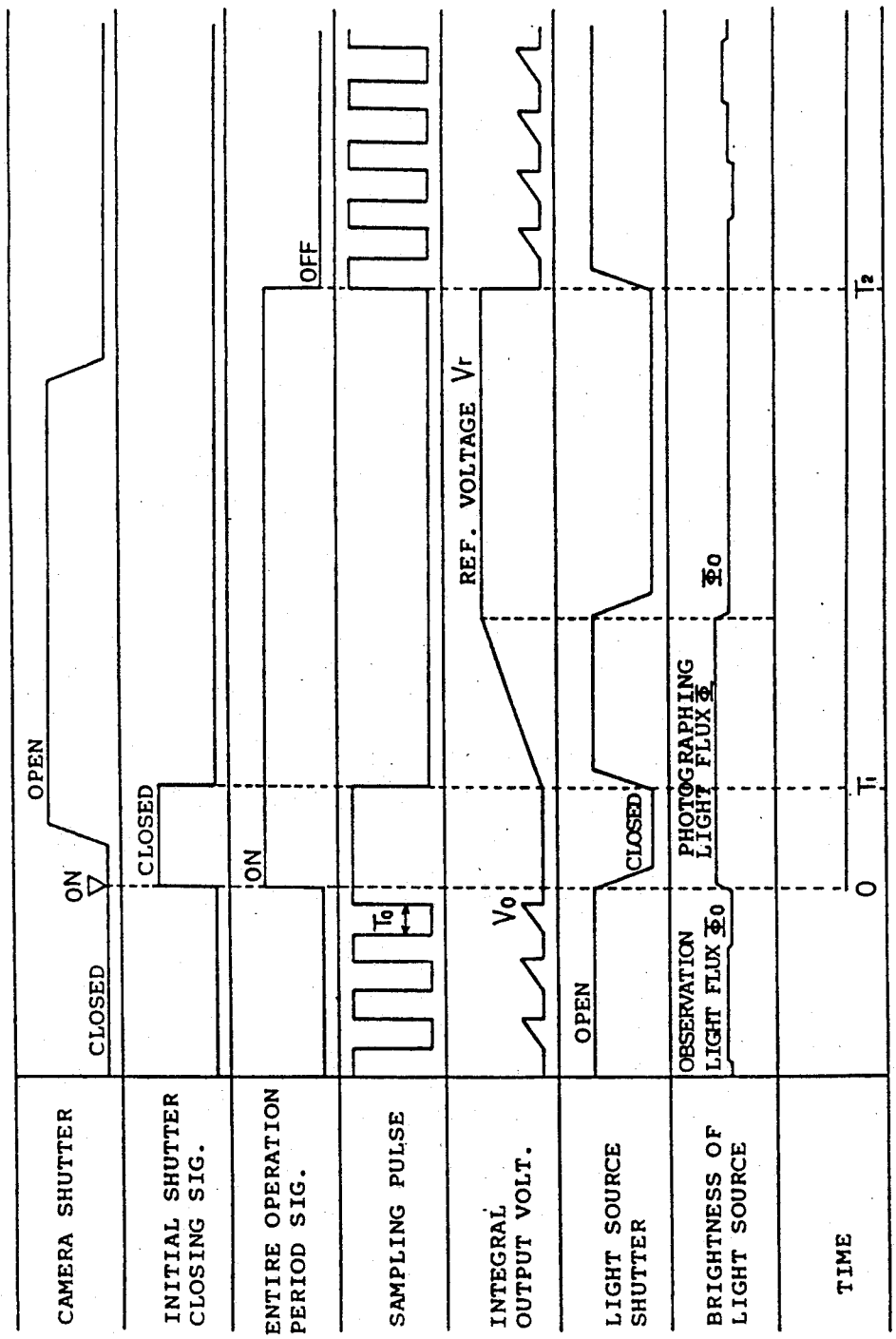
FIG. 3 is a time chart showing the operation of the first embodiment.

FIG. 3 is a time chart showing the operation of the first embodiment.

When the synchro switch 21 on the camera 2 is turned on, the shutter (camera shutter) 22 in the camera 2 is opened with a slight delay and is closed after a predetermined time (e.g., 0.25 sec) has elapsed. Meantime, the light source shutter 42 in the light source apparatus 4 is temporarily closed at the same time as the synchro switch 21 is turned on, and after a predetermined short time (the initial shutter closing time $T_1$) has elapsed, the light source shutter 42 is opened again. The initial shutter closing time $T_1$ is, for example, 0.035 sec. from the moment the synchro switch 21 is turned on.

Before the synchro switch 21 of the camera 2 is turned on during an observation sampling period, an illuminating light flux that corresponds to a brightness level $\Phi_o$ through the brightness setting switch 47 is constantly supplied to the endoscope 1 from the light source apparatus 4. Every time the sampling pulse is at the low level, the output voltage from the light-receiving element 15 is integrated, and the peak value of the integral output voltage that is sampled in the sample-and-hold circuit 62 is selected in the multiplexer 61 and inputted to the CPU 51.

The illuminating light flux $\Phi$ during a photographing operation is controlled by varying either or both the brightness of light that is emitted from the light source 40 and the degree of opening of the variable diaphragm 43 on the basis of the peak value $V_o$ of the integral output voltage that is sampled immediately before the synchro switch 21 is turned on.

More specifically, the photographing light flux $\Phi$ is, for example, set as follows:

$$\Phi = \Phi_o \cdot (T_o \cdot V_r)/(T_f V_o) \qquad (1)$$

where
- $V_o$: the peak value of the integral output voltage sampled immediately before the synchro switch is turned on
- $\Phi_o$: an illuminating light flux (brightness) during the observation sampling period
- $T_o$: an integration execution time determined by the sampling pulse
- $T_f$: an ideal exposure time for photographing (e.g., 0.01 sec)
- $V_r$: a reference voltage In this way, an illuminating light flux Φ for photographing is calculated in synchronism with the closing of the light source shutter 42. After the illuminating light flux has been controlled to the calculated level Φ, the integral state value is directly selected by the multiplexer 61 and input to the CPU 51 from the photometric circuit 19 without passing through the sample-and-hold circuit 62.

It should be noted that the reference voltage $V_r$ is a voltage that is set in proportion to the quantity of exposure light, which is used for a comparison with the integral output voltage V from the light-receiving element 15 during a photographing operation. When the integral output voltage V reaches the reference voltage $V_r$, the light source shutter 42 is closed.

FIG. 4 shows one example of the setting of the reference voltage $V_r$.

When the light source shutter 42 opens, exposure for photographing is initiated and, at the same time, the integral output voltage V begins to rise continuously. When the voltage V reaches the reference voltage $V_r$, the light source shutter 42 is closed, thus completing the exposure for photographing operation. At the same time, the illuminating light flux emitted from the light source is returned to the observation level $\Phi_o$.

During the period from the instant the light source shutter 42 is closed until the entire operation terminating time $T_2$ is reached, the illuminating light that is supplied to the endoscope 1 is intercepted by the light source shutter 42 and hence no endoscopic operation is conducted. When the entire operation terminating time $T_2$ is reached, all the elements of the system return to the previous observational state. It should be noted that $T_2$ is, for example, 0.5 sec from the moment the synchro switch 21 is turned on.

Figure 5:
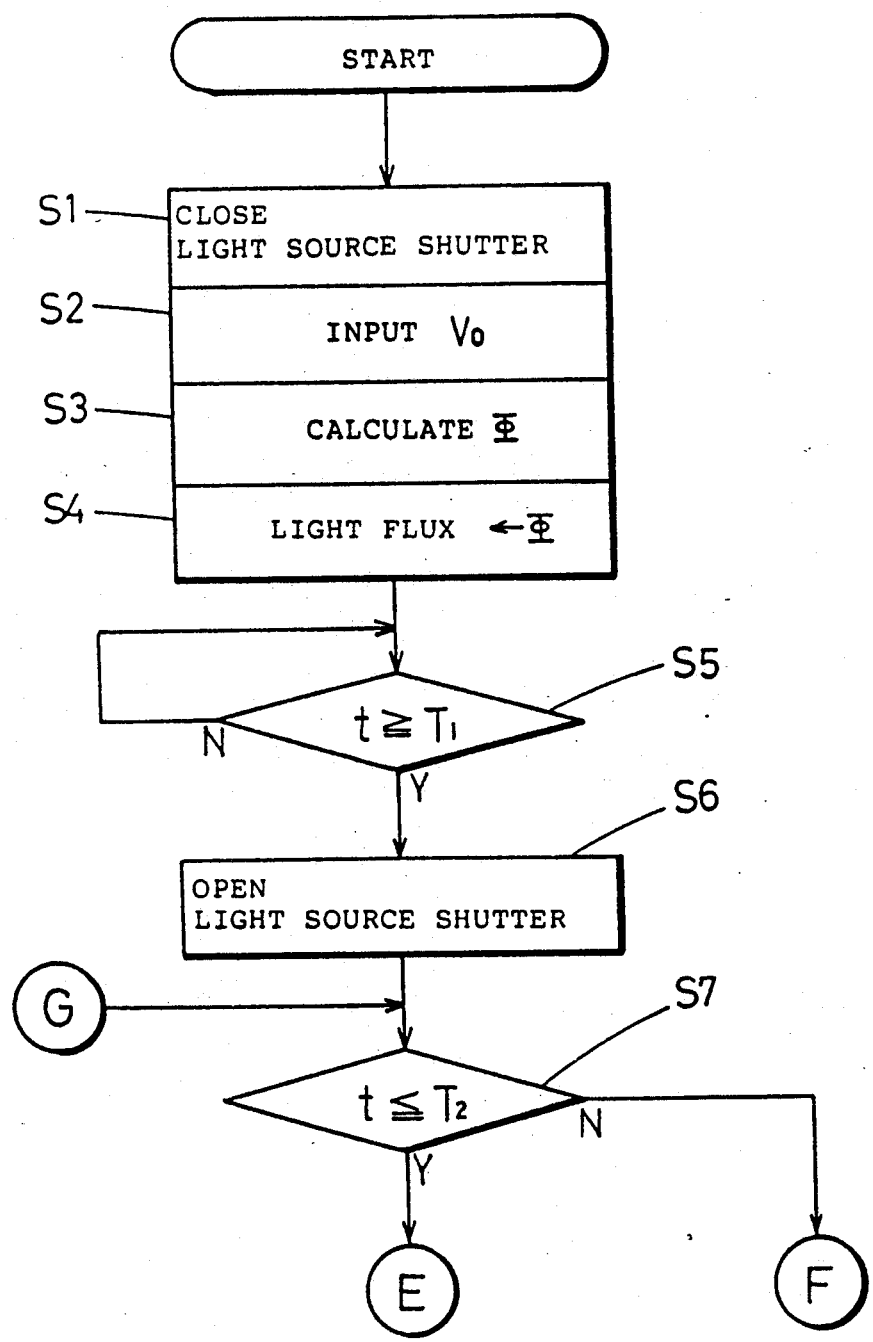
FIGS. 5 and 6 are flowcharts showing a control process in the first embodiment.
Figure 6:
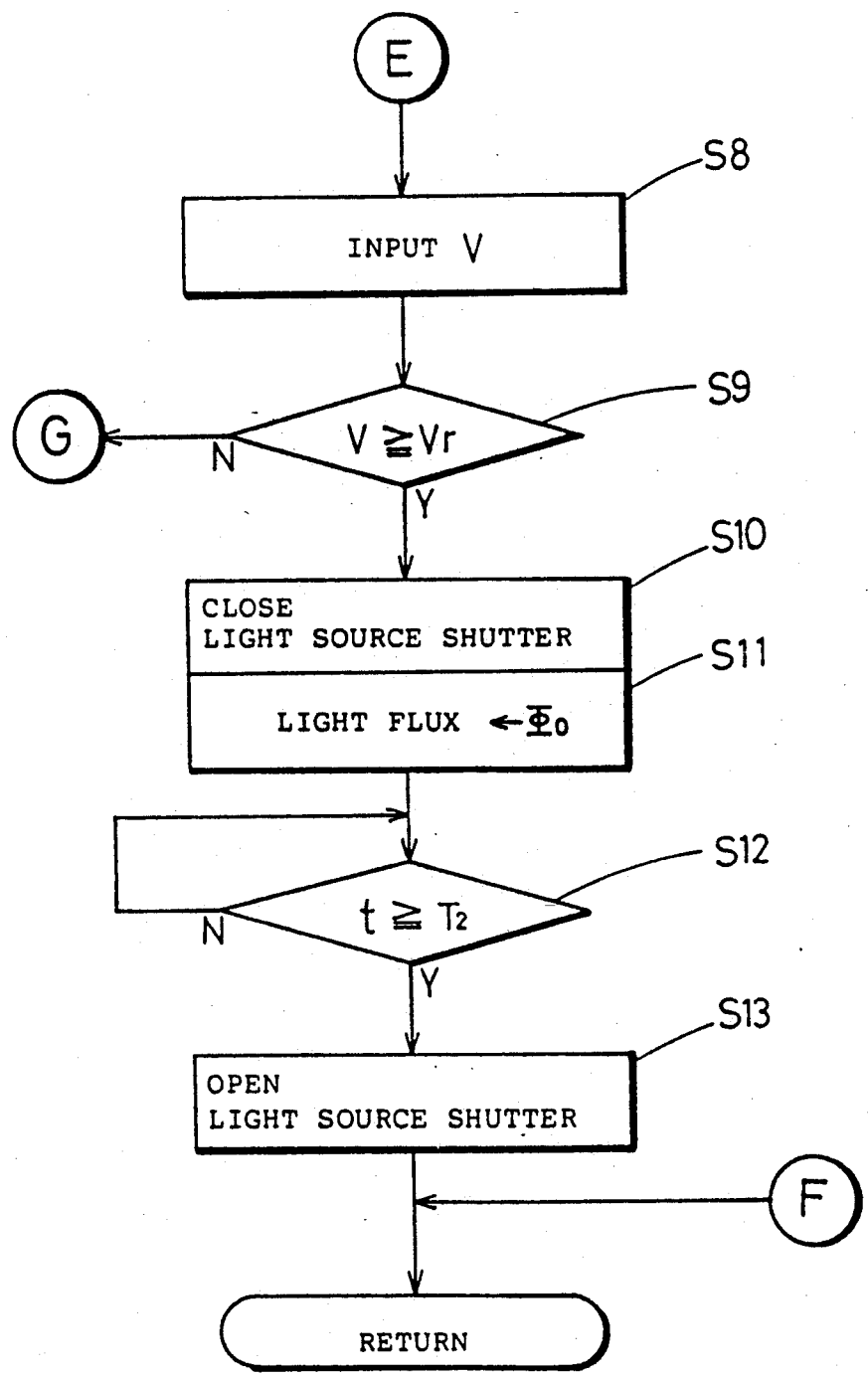

FIGS. 5 and 6 are flowcharts showing a process that is executed in the control section 50 to effect the operation of the above-described embodiment. In the figures, the acronym S denotes Steps.

This process is initiated in response to an interrupt signal that is output when the synchro switch 21 of the camera 2 is turned on during the observation. First, the light source shutter 42 is closed in S1, and $V_o$ (an integral output peak voltage during the observation) immediately before the synchro switch 21 is turned on is input in S2. Then, an illuminating light flux Φ for photographing is calculated according to the equation ① in S3, and either or both the brightness of light that is emitted from the light source 40 and the degree of opening of the diaphragm 43 are controlled in S4 so that the illuminating light flux coincides with the calculated level Φ.

Next, if the time t elapsed since the turning on of the synchro switch 21 reaches $T_1$ in S5, the light source shutter 42 is opened in S6, and the process proceeds to S7. Since $t<T_2$ at the beginning, the integral output voltage V is input in S8. The input of the integral output voltage V is repeated until V reaches the reference voltage $V_r$ in S9. However, if t reaches $T_2$ before V reaches $V_r$, the process returns to the previous observational state from S7.

When V reaches the reference voltage $V_r$ before t reaches $T_2$, the light source shutter 42 is closed in S10, and the illuminating light flux is returned to the previous level $\Phi_o$ for the observation in S11, the process proceeds to S12. When t reaches $T_2$, the light source shutter 42 is opened in S13, and the system then returns to the previous observational state.

Thus, according to the present invention, a brightness level of illuminating light for photographing is calculated from an integral state value based on the observation light, which is sampled immediately before the photographing operation is initiated, and the brightness of illuminating light is controlled to the calculated level. Accordingly, the brightness of illuminating light during the photographing operation can be accurately controlled to the most suitable level for photographing, so that it is possible to control the exposure time to an ideal value. Thus, it is possible to prevent both overexposure and blur and obtain clear, high-quality pictures.

Figure 7:
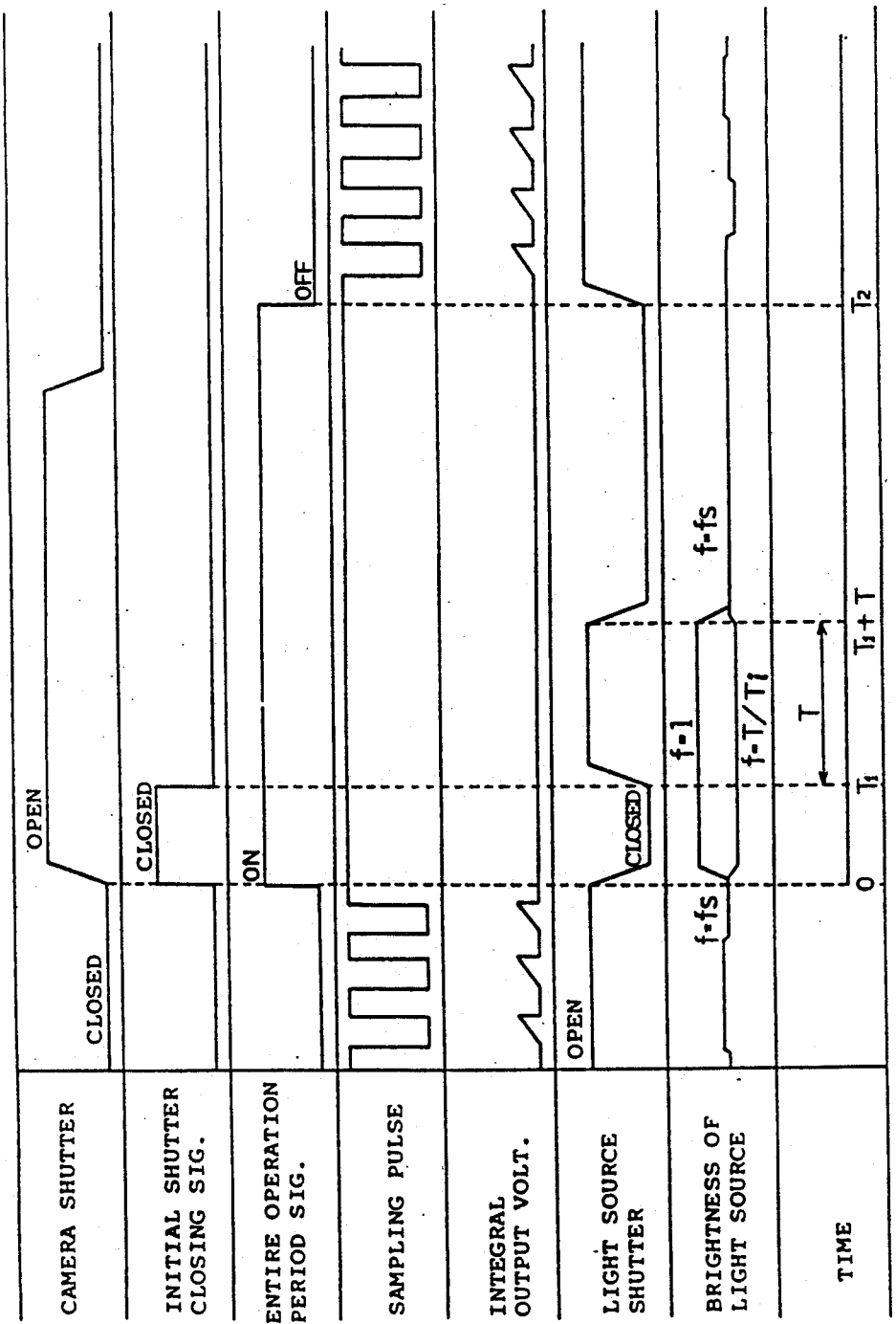
FIG. 7 is a time chart showing the operation of a second embodiment of the present invention.

FIG. 7 is a time chart showing the operation of a second embodiment of the present invention, in which exposure control is effected by software which is different from that in the above-described first embodiment. The same hardware that is used in the first embodiment may be employed in this embodiment.

In this embodiment also, before the synchro switch 21 of the camera 2 is turned on, that is, during the observation, an illuminating light flux that corresponds to a brightness level set through the brightness setting switch 47 is constantly supplied to the endoscope 1 from the light source apparatus 4. Every time the sampling pulse is at the low level, the output voltage from the light-receiving element 15 is integrated, and the peak value of the integral output voltage that is sampled in the sample-and-hold circuit 62 is selected in the multiplexer 61 and input to the CPU 51.

In addition, a rate of change dV/dt of the integral output voltage V per unit time, in the observation state immediately before a photographing operation, is calculated on the basis of the last peak value of the integral output voltage, and an exposure time T is determined on the basis of the calculated value. The light source shutter 42 is closed when the time T has elapsed.

It is assumed that the integration execution time based on the sampling pulse is $T_s$, the integral output voltage is $V_s$, and the aperture value of the variable diaphragm 43 at this time is set at $f_s$. In this case, $f_s$ is somewhere between 0 and 1; 0 representing a fully closed state, and 1 representing a fully open state. A reference voltage is determined through the exposure index setting switch 45 is, an ideal exposure time (e.g., $T_i=0.01$ sec) is determined, and the exposure time is T (when the diaphragm 43 is fully opened), $$dV/dt = V_s/T_s$$

$$T = f_s V_r/(dV/dt)$$

(1) When $T \geq T_i$, the variable diaphragm 43 is fully opened, the exposure time T remains as determined according to the above equation.

(2) However, when $T<T_i$, the aperture value is set to $f=T/T_i$, and to compensate for the change in the degree of opening of the variable diaphragm 43, the exposure time T is set to equal $T_i$.

In either case, the light source shutter 42 is opened during the exposure time T and closed when it has elapsed.

Figure 8:
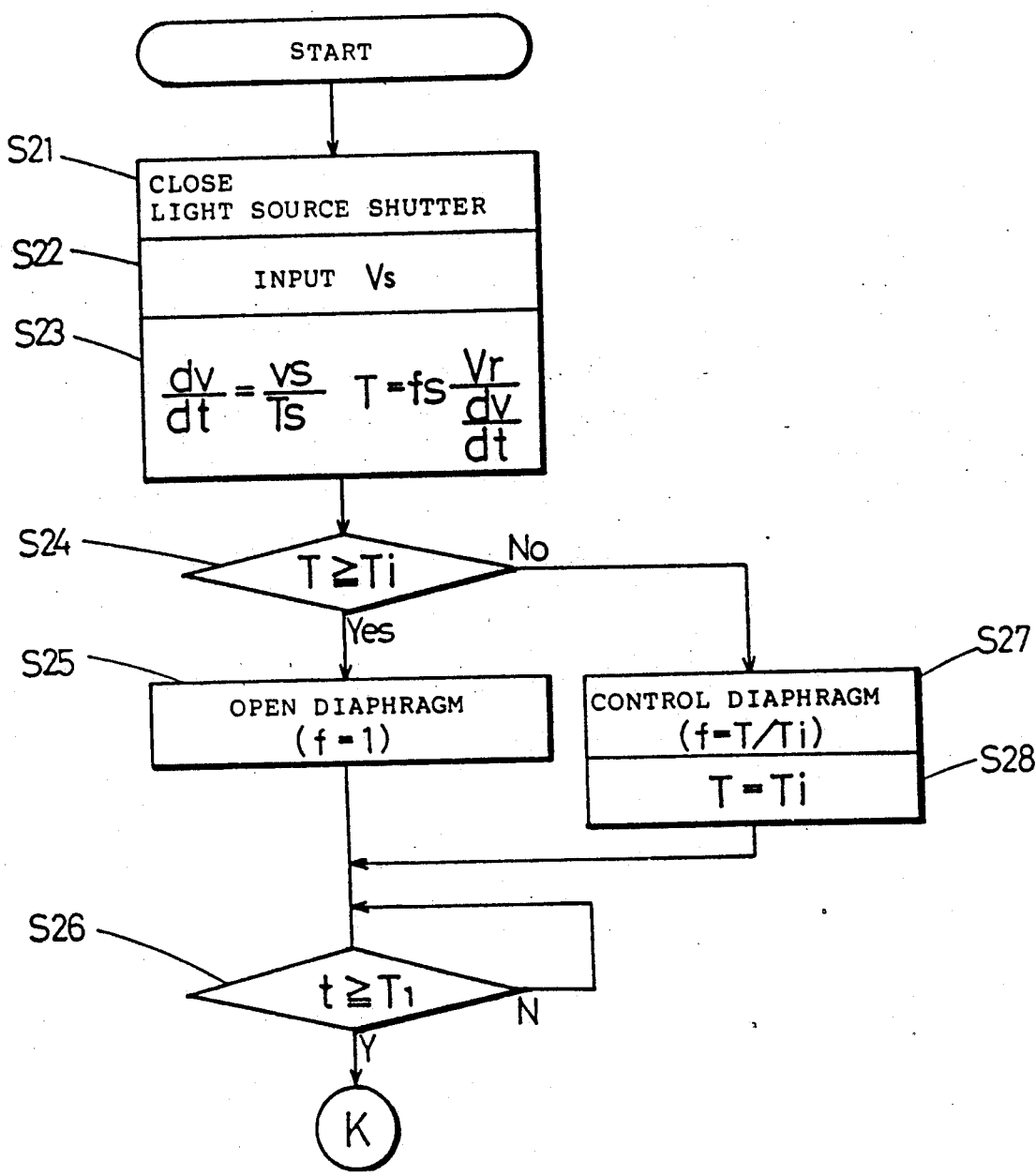
FIGS. 8 and 9 are flowcharts showing a control process in the second embodiment.
Figure 9:
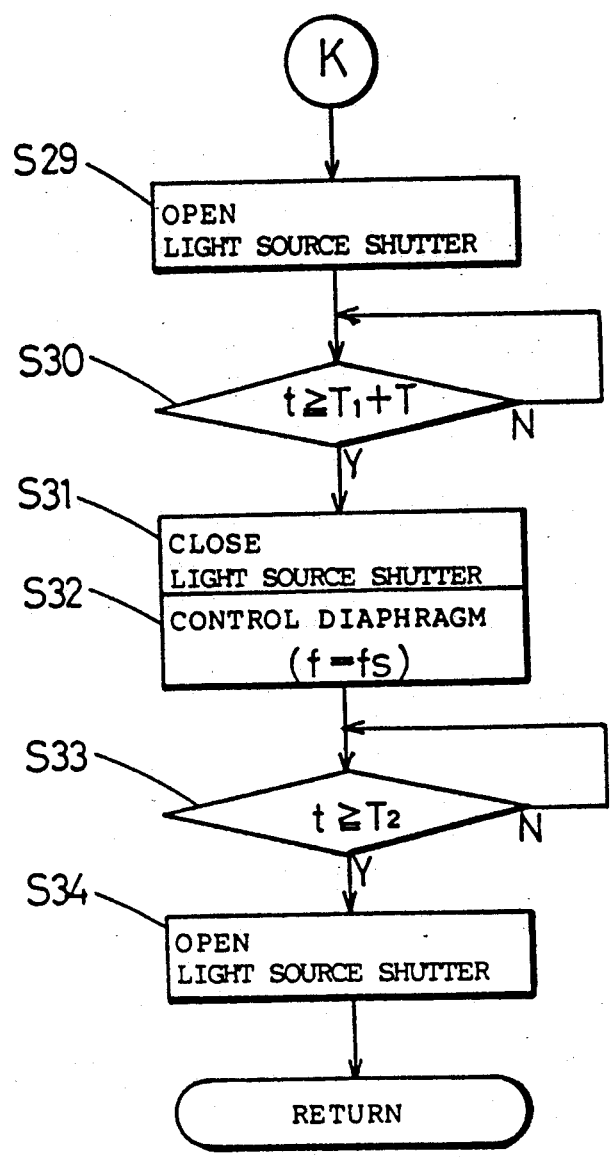

FIGS. 8 and 9 are flowcharts showing a process that is executed in the control section 50 to effect the operation of the second embodiment. In the figures, S denotes Steps.

This process is initiated in response to an interrupt signal that is output when the synchro switch 21 of the camera 2 is turned on during the observation. First, the light source shutter 42 is closed in S21, and the integral output voltage $V_s$, that is sampled in response to a sampling pulse occurring immediately before the photographing operation, is input in S22. Then, a rate of change of the integral output voltage V per unit time, dV/dt, and an exposure time T are calculated in S23.

If the exposure time T is equal to or longer than the ideal exposure time $T_i$ in S24, the variable diaphragm 43 is fully opened, that is, f=1, in S25, and then the process proceeds to S26. If the exposure time T is less than the ideal exposure time $T_i$ in S24, the aperture value of the variable diaphragm 43 is set to $f=T/T_i$, in S27, and $T_i$ is substituted for the exposure time T in S28. Then, the process proceeds to S26.

When the initial shutter closing time $T_1$ has elapsed in S26, the light source shutter 42 is opened in S29. When the exposure time T has elapsed since the light source shutter 42 began to open, the light source shutter 42 is closed in S31. At the same time, the variable diaphragm 43 is returned to the aperture value in the observation state, that is, $f=f_s$, in S32.

Then, when the entire operation terminating time $T_2$ is reached in S33, and the camera shutter has been closed the light source shutter 42 is opened in S34, thus completing the operation.

Thus, according to the present invention, a brightness level of illuminating light for photographing is calculated from an integral state value based on the observation light, which is sampled immediately before the photographing operation is initiated, and the brightness of the illuminating light is controlled to the calculated level. Accordingly, the brightness of illuminating light during the photographing operation can be accurately controlled to the most suitable level for the photographing. In addition, since the exposure time has already been calculated before the photographing operation, the exposure time can be accurately controlled regardless of it amount. Thus, it is possible to prevent both over-exposure and blur and obtain clear, high-quality pictures.

Figure 10:
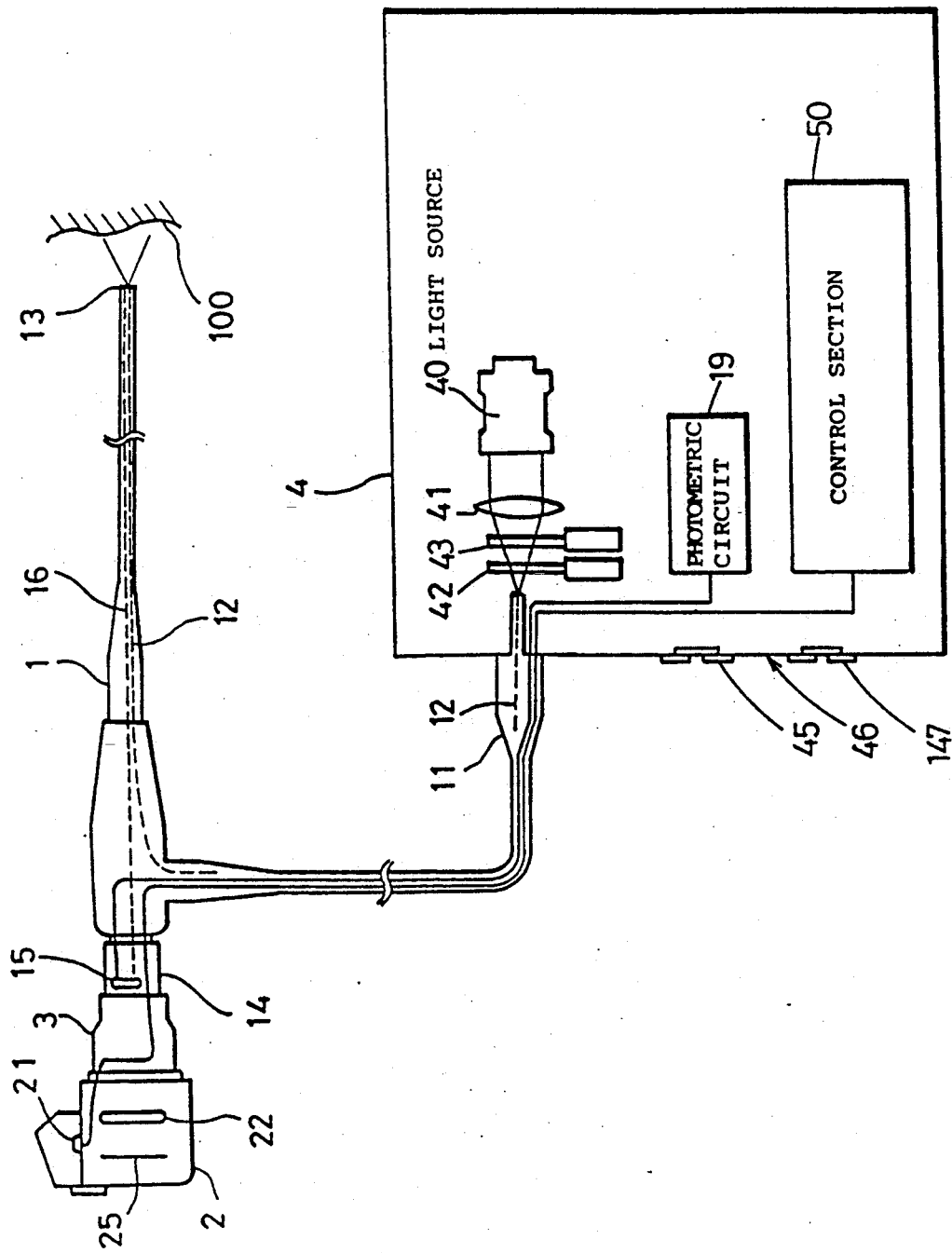
FIG. 10 is a schematic view showing the a complete arrangement of a third embodiment of the present invention.

FIG. 10 shows the whole arrangement of a third embodiment of the present invention. The arrangement is the same as that shown in FIG. 1 except that a brightness index setting switch 147 is provided in place of the brightness setting switch 47.

Reference numeral 45 denotes an exposure index setting switch, which is provided on an operation panel 46 that is attached to the surface of the light source apparatus 4 to set an exposure index EI that determines a quantity of light which is to be applied to the photographic plane 25 in the camera 2. The exposure index setting switch 45 is provided such that the exposure quantity can be controlled in units of 0.5 on the EV scale, as exemplarily shown in FIG. 11.

The brightness index setting switch 147 is used to set a brightness of illuminating light supplied to the endoscope 1 in the observation state in accordance with the distance from the distal end 13 of the insert part to the object 100 or in accordance with other conditions. More specifically, the brightness of illuminating light (i.e., the illuminating light flux that is supplied to the endoscope 1) during the observation can be controlled by the brightness index BI in units of 0.5 on the EV scale, as exemplarily shown in FIG. 12.

It should be noted that Te and Tb numbers that are shown in FIGS. 11 and 12 are integral numbers which are adopted in this embodiment, with a view to simplifying the calculation.

Figure 13:
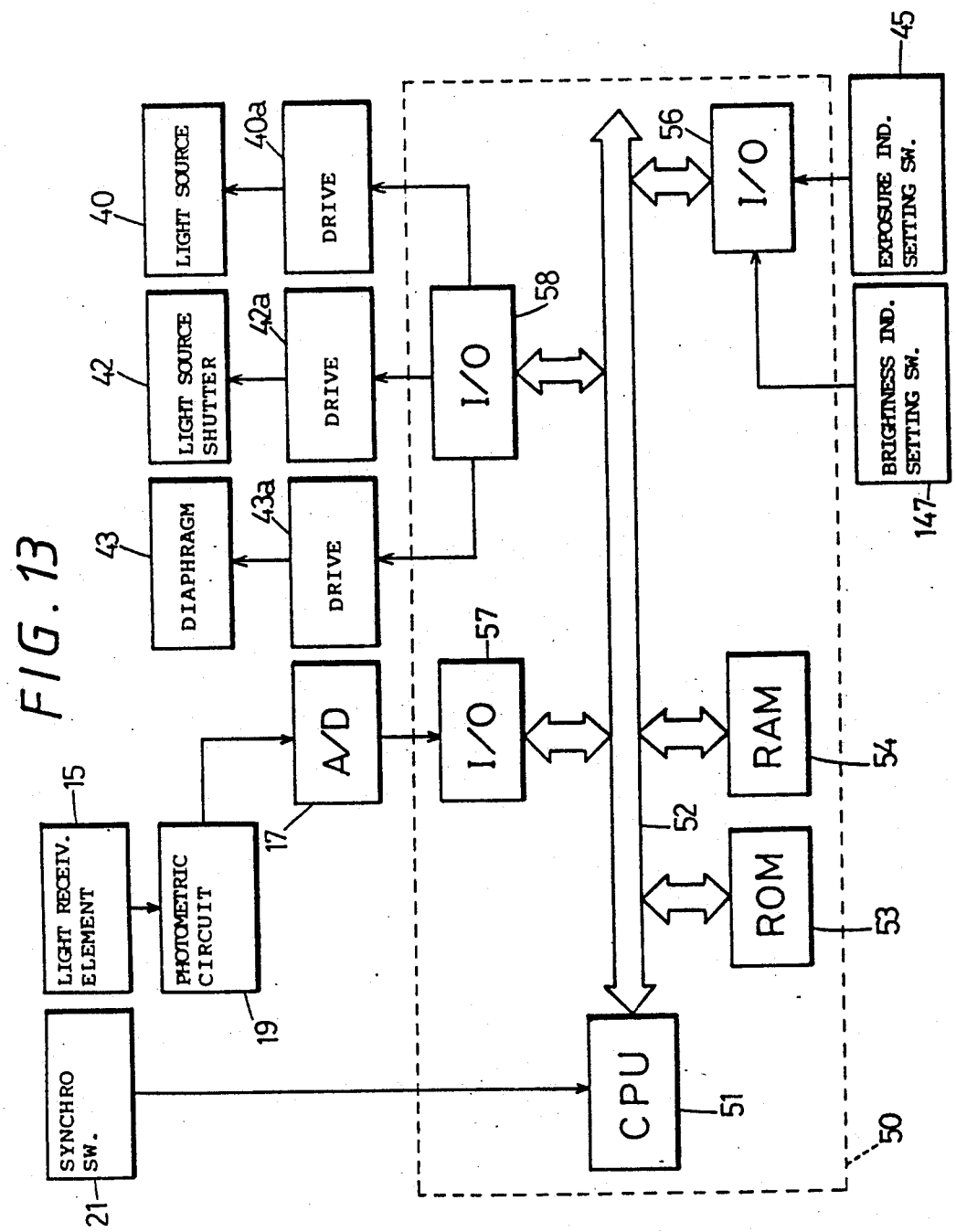
FIG. 13 is an electric circuit block diagram of the third embodiment.

Referring to FIG. 13, which is a block diagram showing the electrical arrangement of the third embodiment, the control section 50 includes a central processing unit (CPU) 51. A read only memory (ROM) 53 and a random access memory (RAM) 54 are connected to the CPU 51 through a system bus 52. The CPU 51 is supplied with an interrupt signal which is outputted from the synchro switch 21.

The system bus 52 is further connected with first to third input/output ports 56, 57 and 58. The exposure index setting switch 45 and the brightness index setting switch 147 are connected to the input terminal of the first input/output port 56. Although in this embodiment the brightness index BI is set by a manual operation in accordance with the distance to the object 100, the arrangement may be such that the brightness index BI is set automatically.

The output from the light-receiving element 15 is integrated in the photometric (integration) circuit 19 to obtain an integral state value (integral output voltage V), which is input to the input terminal of the second input/output port 57 through an analog-to-digital converter 17. The output terminal of the third input/output port 58 is connected to drivers 40a, 42a and 43a which control the brightness of light that is emitted from the light source 40, the opening and closing operation of the light source shutter 42, and the degree of opening of the variable diaphragm 43, respectively.

The system is further provided with an initial shutter closing signal generator which generates a signal for closing the light source shutter 42 for a predetermined short time $T_1$ in response to the turn on of the synchro switch 21, and a signal generator which generates an entire operation period signal that defines the entire operation period $T_2$ of the system in response to the turn on of the synchro switch 21. Output signals from these generators are inputted to the control section 50. Illustration of these generators is, however, omitted.

Figure 14:
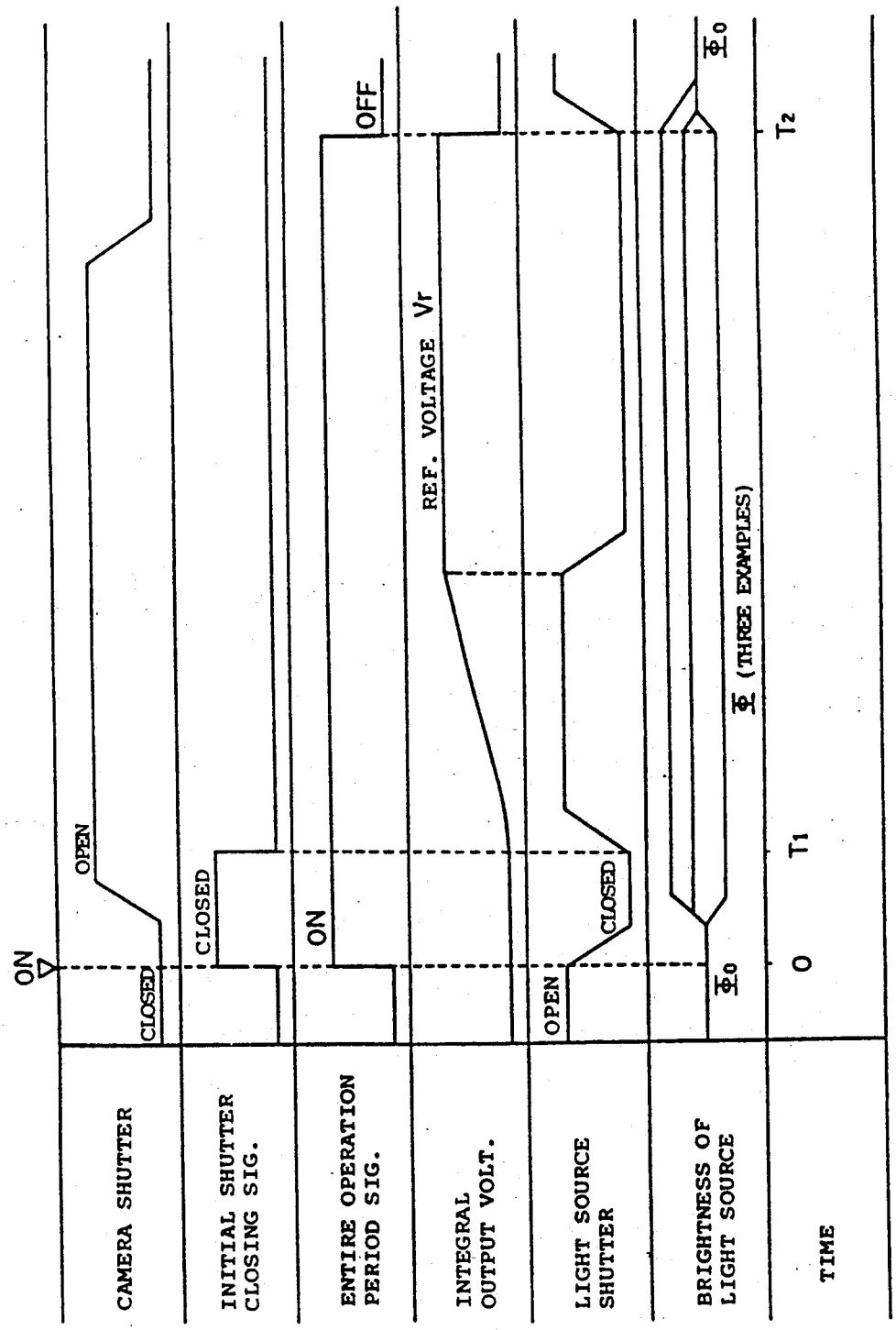
FIG. 14 is a time chart showing the operation of the third embodiment.

FIG. 14 is a time chart showing the operation of the third embodiment.

When the synchro switch 21 on the camera 2 is turned on, the shutter (camera shutter) 22 in the camera 2 is opened with a slight delay and is closed after the predetermined time $T_1$ (e.g., 0.25 sec) has elapsed. Meantime, the light source shutter 42 in the light source apparatus 4 is temporarily closed in response to an initial shutter closing signal which is outputted at the same time as the synchro switch 21 is turned on. In addition, an entire operation period signal is turned on.

After the relatively short time $T_1$, the initial shutter closing signal falls and, at the same time, the light source shutter 42 begins to open.

Prior to this, when the light source shutter 42 is closed, the illuminating light flux Φ for photographing is controlled by varying either or both the brightness of light that is emitted from the light source 40 and the degree of opening of the variable diaphragm 43.

The photographing light flux Φ is calculated on the basis of the above-described exposure index EI and brightness index BI. The calculation of the photographing light flux Φ will be explained below by way of specific examples.

As shown in FIGS. 11 and 12, the exposure index EI may be set in the light source apparatus 4 within a range of from 0 to 9, and similarly the brightness index BI is set within a range of from 0 to 9. It may be assumed that an ideal shutter speed (e.g., 0.01 sec) of the light source shutter 42 that provides a correct exposure is obtained on condition that a standard exposure index EI and a standard brightness index BI are 5 each, the object 100 is at a standard distance (e.g., 20 mm from the distal end 13 of the insert part) and the illuminating light flux that is supplied to the endoscope 1 during photographing is at a standard brightness level $\Phi_s$. Under these conditions, an illuminating light flux $\Phi$ for photographing is set as follows:

$$\Phi = \Phi_s \cdot 2^{(5-EI)/2} \cdot 2^{(BI-5)/2k}$$

where k is a constant ($k \geq 1$)

In this way, $\Phi$ is calculated, and the illuminating light flux is controlled to the calculated value. Thus, in the above-described standard state, where EI and BI are each 5, $\Phi = \Phi_s$, and the light source shutter 42 is closed after 0.01 sec has elapsed.

When the exposure index EI is larger than that in the standard state (that is, when photographing of correct exposure is attained with a smaller amount of exposure light) or when the brightness index BI is smaller than that in the standard state (that is, when the illuminating light flux during the observation is reduced because the distance to the object 100 is relatively short), $\Phi$ decreases, so that the exposure time will not needs to be shortened and no over-exposure will occur.

Conversely, when the exposure index EI is smaller than that in the standard state (that is, when a larger amount of exposure light is needed to perform photographing with a correct exposure) or when the brightness index BI is larger than that in the standard state (that is, when the illuminating light flux during the observation is increased because the distance to the object 100 is relatively long), $\Phi$ increases, so that the exposure time will not needs to be increased and no blur will occur.

The following is the reason why k in the equation used to determine $\Phi$ is a constant that is not less than 1:

As to the exposure index EI, the numerical value thereof is exactly reflected in the exposure time, so that, for each difference of 1 between adjacent integers in the table shown in FIG. 11, the exposure time should be increased exactly by $2^{\frac{1}{2}}$ times or $2^{-\frac{1}{2}}$ times. However, the brightness index BI is not always exactly reflected in the exposure time. In general, the effect of BI is smaller than that of EI. For this reason, $k \geq 1$ is employed to reduce the effect of BI in comparison to that of EI on the determination of an illuminating light flux $\Phi$ for photographing.

The value for k may be determined by photographic experiment, for example. FIG. 12 shows Tb numbers in a case where k is set to 2, for example. In this case $\Phi$ is given by $$\Phi = \Phi_s \cdot 2^{(Tc+Tb-16)/4}$$

Figure 15:
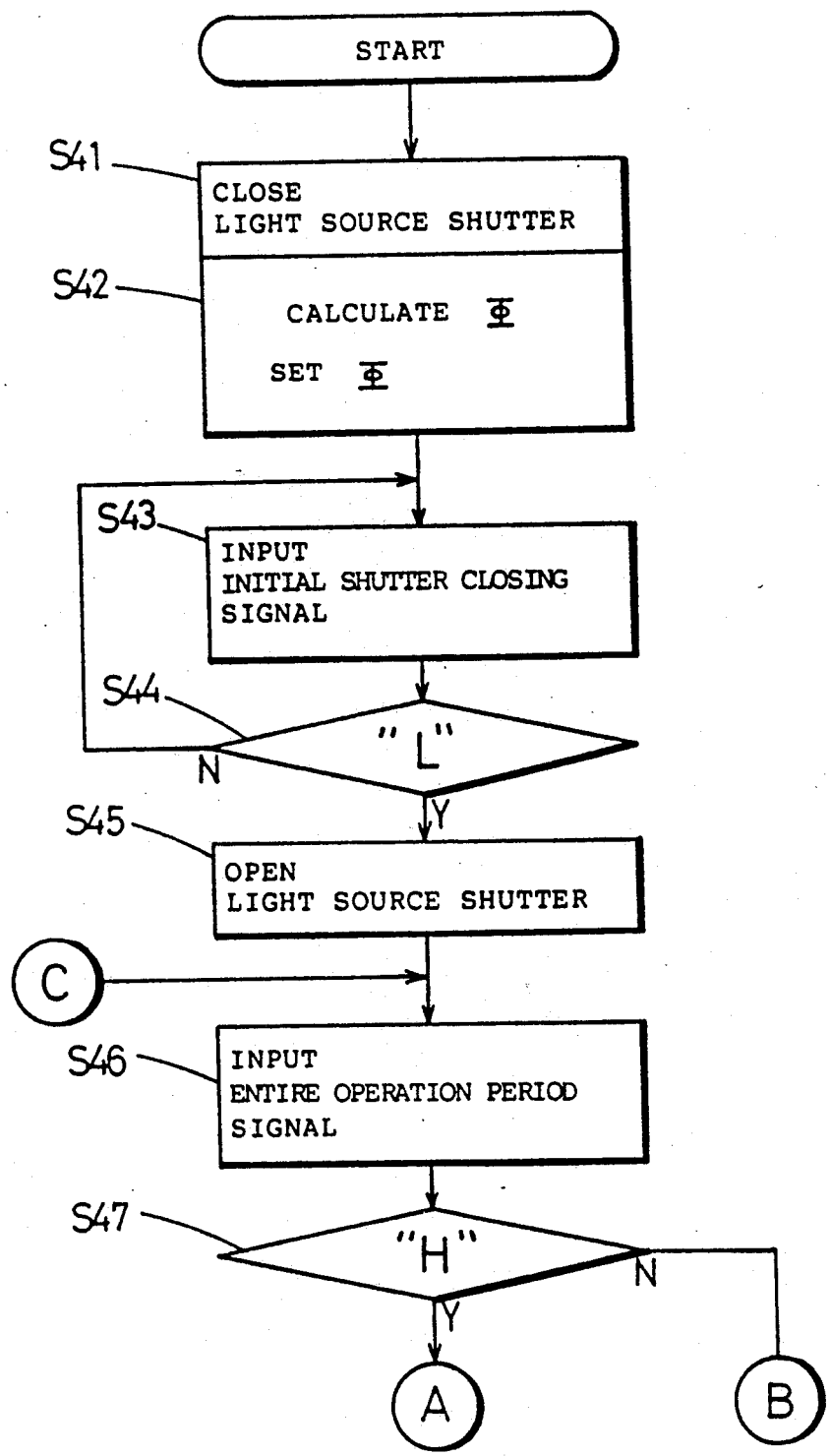
FIGS. 15 and 16 are flowcharts showing a control process in the third embodiment.
Figure 16:
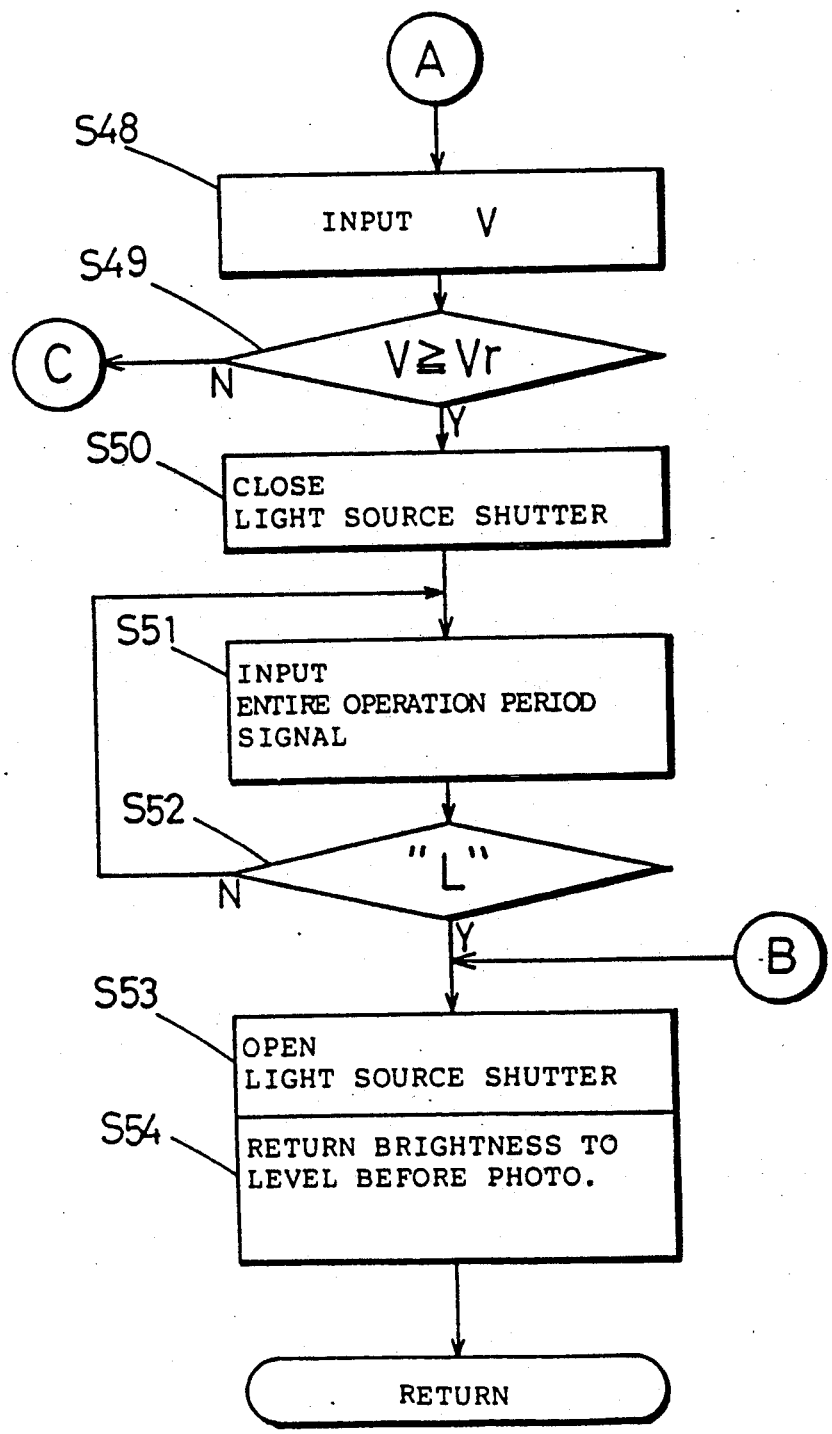

FIGS. 15 and 16 are flowcharts showing a process that is executed in the control section 50 to effect the operation of the third embodiment. In the figures, S denotes Steps.

This process is initiated when the synchro switch 21 of the camera 2 is turned. First, the light source shutter 42 is closed in S41. Subsequently, $\Phi$ is calculated and either or both the brightness of light that is emitted from the light source 40 and the degree of opening of the variable diaphragm 43 are controlled in S42 so that the calculated value is actually obtained as an illuminating light flux.

Then, the initial shutter closing signal is inputted in S43. If the signal is not at the low level in S44, the process returns to S43 to repeat the sequence from the input of the initial shutter closing signal. When the signal becomes low in level in S44, the light source shutter 42 is opened in S45.

Subsequently, the entire operation period signal is inputted in S46, and if the signal is not at the high level in S47, the process proceeds to S53, whereas, if the signal is at the high level, the integral output voltage V is input in S48, and it is judged in S49 whether or not V has reached the reference voltage $V_r$.

If V is lower than $V_r$ in S49, the sequence is repeated from S46. When $V \geq V_r$, the light source shutter 42 is closed in S50. Then, the entire operation period signal is input in S51. If the signal is not at the low level in S52, the process returns to S51 to repeat the sequence from the input of the entire operation period signal, whereas, if the signal is at the low level in S52, the process proceeds to S53.

Finally, the light source shutter 42 is opened in S53, and the illuminating light flux is returned to the level before the photographing operation in S54, thus completing the operation.

Thus, according to the present invention, a brightness level of illuminating light for photographing is calculated from both the exposure index and the brightness of illuminating light during the observation, and the brightness of the illuminating light is controlled to the calculated level when a photograph is taken. Accordingly, the exposure time can be controlled to an ideal value by delicately controlling the brightness of illuminating light for photographing. Thus, it is possible to prevent both over-exposure and blur and obtain clear, high-quality pictures.

While the invention has been described by reference to specific embodiments chosen for purposes of illustration, it should be apparent that numerous modifications could be made thereto by those skilled in the art without departing from the basic concept and scope of the invention.

We claim:

1. A photographing light quantity controller for an endoscope, which is used to control the quantity of illuminating light when a photograph is to be taken through said endoscope, said controller comprising:
   a light source for supplying light, for illuminating an object to said endoscope;
   means for initiating and synchronizing a photographing operation;
   detecting means for detecting an illuminating condition in an observation state before a photographing operation is initiated and synchronized by said means for initiating; and
   control means for charging the brightness of illuminating light that is supplied from said light source to said endoscope during the photographing operation on the basis of a signal that is detected by said means for detecting an illuminating condition in the observation state.

2. A photographing light quantity controller for an endoscope according to claim 1, wherein said control means controls the brightness of light that is emitted from said light source.

3. A photographing light quantity controller for an endoscope according to claim 1, wherein said control means has a variable diaphragm that intercepts the path of illuminating light supplied from said light source to said endoscope.

4. A photographing light quantity controller for an endoscope according to claim 1, wherein said detecting means for detecting an illuminating condition in an observation state before a photographing operation is initiated has a photoelectric conversion means for converting into an electric signal a brightness level of exposure light that is applied to a photographic plane in a photographing device after being reflected from said object.

5. A photographing light quantity controller for an endoscope according to claim 4, wherein said detecting means for detecting an illuminating condition in an observation state before a photographing operation is initiated further has integrating means for repeatedly integrating for a short time period an output signal from said photoelectric conversion means during the observation state and outputting the resulting integral value.

6. A photographing light quantity controller for an endoscope according to claim 5, wherein said control means calculates a brightness level of illuminating light for a photographing operation from an integral value that is output from said integrating means immediately before the photographing operation is initiated, and controls the brightness of illuminating light, supplied to said endoscope during the photographing operation, to be said calculated brightness level.

7. A photographing light quantity controller for an endoscope according to claim 1, further comprising observation light brightness setting means for setting a brightness level of illuminating light that is supplied to said endoscope in an observation state, said control means calculating a brightness level of illuminating light for a photographing operation from the brightness level set by said setting means, and controlling the brightness of illuminating light supplied to said endoscope during the photographing operation on the basis of the calculated brightness level.

8. A photographing light quantity controller for an endoscope according to claim 7, further comprising exposure index setting means for setting an exposure index that determines a quantity of exposure light that is applied to a photographic plane in a photographing device after being reflected from said object, said control means calculating a brightness level of illuminating light for a photographing operation from an exposure index that is set by said exposure index setting means and the brightness level set by said observation light brightness setting means, and controlling the brightness of illuminating light supplied to said endoscope during the photographing operation on the basis of the calculated brightness level.

9. A photographing light quantity controller for an endoscope according to claim 1, wherein said control means controls both the brightness of illuminating light that is supplied from said light source to said endoscope during the photographing operation and the exposure time on the basis of a signal that is detected by said detecting means.

10. A photographing light quantity controller for an endoscope according to claim 9, wherein said detecting means has photoelectric conversion means for converting, into an electric signal, a brightness level of exposure light that is applied to a photographic plane in a photographing device after being reflected from said object.

11. A photographing light quantity controller for an endoscope according to claim 10, wherein said detecting means further has integrating means for repeatly integrating, for short time periods, an output signal from said photoelectric conversion means during the observation state and outputting the resulting integral state value.

12. A photographing light quantity controller for an endoscope according to claim 11, wherein said control means calculates a brightness level of illuminating light for a photographing operation and an exposure time from an integral value that is outputted from said integrating means immediately before the photographing operation is initiated, and controls the brightness of illuminating light that is supplied from said light source to said endoscope and the exposure time during the photographing operation on the basis of the calculated values.

13. A photographing light quantity controller for an endoscope according to the claim 1, wherein said detecting means comprises photoelectric conversion means for converting a brightness level of said illuminating light into an electric signal.

14. A photographing light quantity controller for an endoscope according to claim 9, wherein said detecting means comprises photoelectric conversion means for converting a brightness level of said illuminating light into an electric signal.

15. A photographing apparatus comprising:
a light source for supplying light, for illuminating an object to be photographed by said photographing apparatus;
means for initiating and synchronizing a photographing operation;
detecting means for detecting an illuminating condition before a photographing operation is initiated and synchronized by said means for initiating; and
control means for controlling the brightness of illuminating light that is supplied from said light source to said endoscope during the photographing operation on the basis of a signal that is detected by said detecting means for detecting an illuminating condition in the observation state.

16. A photographing apparatus according to claim 15, wherein said detecting means detects an illuminating condition while said photographing apparatus is in an observation state.

17. A photographing apparatus according to claim 15, wherein said means for initiating comprises means for activating a plurality of operations of said photographing apparatus pertaining to said photographing operation.

18. A photographing light quantity controller for an endoscope according to claim 1, wherein said control means comprises means for adjusting the brightness of the illuminating light that is supplied from said light source to one of a plurality of brightness levels.

* * * * *

UNITED STATES PATENT AND TRADEMARK OFFICE
CERTIFICATE OF CORRECTION

PATENT NO. : 5,184,170
DATED : February 2, 1993
INVENTOR(S) : T. TAKAHASHI et al.

It is certified that error appears in the above-indentified patent and that said Letters Patent is hereby corrected as shown below:

On the title page, in section [30], Foreign Application Priority Data, line 3, change "2-20055" to ---2-200055---.

At column 10, line 54 (claim 1, line 13) of the printed patent, change "charging" to ---changing---.

At column 12, line 6 (claim 11, line 3) of the printed patent, change "repeatly" to ---repeatedly---.

At column 12, line 15 (claim 12, line 5) of the printed patent, change "outputted" to ---output---.

Signed and Sealed this

Seventeenth Day of September, 1996

Attest:

BRUCE LEHMAN

*Attesting Officer*    *Commissioner of Patents and Trademarks*